United States Patent
Velschow

(10) Patent No.: US 10,286,149 B2
(45) Date of Patent: May 14, 2019

(54) BODY FLUID SAMPLING DEVICE AND A METHOD THEREOF

(75) Inventor: Sten Velschow, Vedbaek (DK)

(73) Assignee: FluiSense ApS, Allerod (DK)

( * ) Notice: Subject to any disclaimer, the term of this patent is extended or adjusted under 35 U.S.C. 154(b) by 1237 days.

(21) Appl. No.: 13/132,819

(22) PCT Filed: Dec. 2, 2009

(86) PCT No.: PCT/DK2009/050317
§ 371 (c)(1),
(2), (4) Date: Jul. 21, 2011

(87) PCT Pub. No.: WO2010/063290
PCT Pub. Date: Jun. 10, 2010

(65) Prior Publication Data
US 2012/0017999 A1    Jan. 26, 2012

(30) Foreign Application Priority Data
Dec. 5, 2008 (DK) .......... PA 2008 017305

(51) Int. Cl.
*A61B 5/00* (2006.01)
*A61M 5/178* (2006.01)
*A61B 5/15* (2006.01)
*A61B 5/155* (2006.01)

(52) U.S. Cl.
CPC .............. *A61M 5/178* (2013.01); *A61B 5/00* (2013.01); *A61B 5/155* (2013.01); *A61B 5/150015* (2013.01); *A61B 5/150221* (2013.01); *A61B 5/150229* (2013.01); *A61B 5/150358* (2013.01); *A61B 5/150755* (2013.01); *A61B 5/150992* (2013.01); *Y10T 137/0318* (2015.04); *Y10T 137/8593* (2015.04); *Y10T 137/85978* (2015.04)

(58) Field of Classification Search
CPC ...................................................... A61B 5/00
USPC ......... 600/573, 576, 578, 581, 582; 604/504
See application file for complete search history.

(56) References Cited

U.S. PATENT DOCUMENTS

| | | | | |
|---|---|---|---|---|
| 3,894,701 A | | 7/1975 | Moscaret et al. ............. | 242/194 |
| 3,908,657 A | * | 9/1975 | Kowarski ...................... | 600/580 |
| 4,127,111 A | * | 11/1978 | Drolet .......................... | 600/573 |
| 4,218,421 A | * | 8/1980 | Mack et al. .................... | 422/66 |
| 4,667,854 A | | 5/1987 | McDermott et al. ......... | 222/101 |
| 4,871,439 A | * | 10/1989 | Enzer et al. .................. | 204/401 |
| 4,919,596 A | * | 4/1990 | Slate et al. ...................... | 417/18 |
| 4,951,669 A | * | 8/1990 | Maxwell ............. | A61B 5/1459 600/312 |

(Continued)

FOREIGN PATENT DOCUMENTS

| | | |
|---|---|---|
| DE | 19819407 | 11/1999 |
| EP | 1690496 | 8/2006 |

(Continued)

*Primary Examiner* — May A Abouelela
(74) *Attorney, Agent, or Firm* — Seed Intellectual Property Law Group LLP

(57) ABSTRACT

According to an embodiment of the invention, a body fluid sampling device is disclosed. The device includes a channel for allowing passage of the fluid through the channel, a flow controller for maintaining flow of the fluid in the channel; a flow direction controller for changing the direction of the flow of the fluid towards a collection medium; and the flow controller for delivering a portion of the fluid as a sample onto the collection medium.

38 Claims, 13 Drawing Sheets

(56) References Cited

U.S. PATENT DOCUMENTS

| | | | | |
|---|---|---|---|---|
| 5,077,010 | A * | 12/1991 | Ishizaka et al. | 422/408 |
| 5,296,197 | A | 3/1994 | Newberg et al. | 422/103 |
| 5,441,071 | A | 8/1995 | Doherty et al. | 137/15 |
| 5,466,228 | A * | 11/1995 | Evans | 604/248 |
| 5,807,312 | A * | 9/1998 | Dzwonkiewicz | A61M 5/1424 604/248 |
| 6,128,519 | A * | 10/2000 | Say | A61B 5/1495 600/309 |
| 6,296,811 | B1 | 10/2001 | Sasaki | 422/100 |
| 6,988,996 | B2 * | 1/2006 | Roe et al. | 600/584 |
| 7,258,672 | B2 * | 8/2007 | Hansson et al. | 600/581 |
| 7,316,662 | B2 * | 1/2008 | Delnevo | A61M 5/165 604/21 |
| 7,481,787 | B2 * | 1/2009 | Gable et al. | 604/19 |
| 8,052,617 | B2 * | 11/2011 | Kissinger | 600/573 |
| 8,139,207 | B2 * | 3/2012 | Braig et al. | 356/39 |
| 8,251,907 | B2 * | 8/2012 | Sterling | A61B 5/1427 435/283.1 |
| 8,366,690 | B2 * | 2/2013 | Locke et al. | 604/318 |
| 8,425,416 | B2 * | 4/2013 | Brister | A61B 5/14532 600/309 |
| 8,523,797 | B2 * | 9/2013 | Lowery et al. | 604/4.01 |
| 8,597,190 | B2 * | 12/2013 | Rule et al. | 600/366 |
| 2004/0152622 | A1 | 8/2004 | Keith et al. | 514/3 |
| 2005/0015019 | A1 * | 1/2005 | Honda et al. | 600/576 |
| 2006/0074350 | A1 * | 4/2006 | Cash | 600/581 |
| 2006/0079809 | A1 * | 4/2006 | Goldberger et al. | 600/576 |
| 2006/0188407 | A1 * | 8/2006 | Gable | A61B 5/0084 604/19 |
| 2006/0229531 | A1 * | 10/2006 | Goldberger et al. | 600/573 |
| 2007/0006820 | A1 | 1/2007 | Denault et al. | 119/792 |
| 2007/0106134 | A1 * | 5/2007 | O'Neil | A61B 5/083 600/309 |
| 2007/0119710 | A1 * | 5/2007 | Goldberger et al. | 204/403.01 |
| 2007/0191735 | A1 * | 8/2007 | Hansson | 600/573 |
| 2007/0225675 | A1 * | 9/2007 | Robinson | A61B 5/14 604/504 |
| 2008/0275324 | A1 | 11/2008 | Goldberger et al. | 600/365 |
| 2008/0287661 | A1 | 11/2008 | Jones | 530/418 |
| 2009/0299223 | A1 * | 12/2009 | Hirabuki | 600/576 |
| 2010/0021315 | A1 * | 1/2010 | Wolff | 417/53 |
| 2010/0137778 | A1 * | 6/2010 | Kunjan | A61B 5/1427 604/6.15 |

FOREIGN PATENT DOCUMENTS

| | | |
|---|---|---|
| EP | 1953546 A1 | 8/2008 |
| EP | 1722684 | 9/2008 |
| JP | 08-000599 A | 1/1996 |
| JP | 11-244263 A | 9/1999 |
| JP | 2008-194464 A | 8/2008 |
| WO | 2005084547 A1 | 9/2005 |
| WO | 2006/082446 | 8/2006 |
| WO | 2006/132571 | 12/2006 |
| WO | 2007054317 A1 | 5/2007 |
| WO | 2007062225 A2 | 5/2007 |

* cited by examiner

BODY FLUID SAMPLING DEVICE AND A METHOD THEREOF

FIELD OF THE INVENTION

The present invention relates to a sampling device. More particularly, the invention relates to a fluid sampling device and a method thereof.

BACKGROUND OF THE INVENTION

Collection and subsequent analysis of fluid samples is used for monitoring industrial processes, determining properties and dynamics of pharmaceutical, chemical compounds and biological materials in animals and humans and also in natural or artificial systems, for environmental research and surveillance, for monitoring sewage, flowing water in streams and rivers, precipitation.

In medical science and pharmaceutical industry, there is often a need to perform pharmacokinetic studies on living beings, for example test objects such as rats and pigs. In such studies, it is common to take a plurality of samples or specimens from the test object. Also, injecting substances into the test object during the course of hours or days, in order to allow observation of gradual responses in the test object is also common.

Similarly, patient blood chemistry and monitoring of patient blood chemistry are important diagnostic tools in patient care. For example, the measurement of blood analytes and parameters often provide much needed patient information regarding the proper dose and administration time period. Blood analytes and parameters tend to change frequently, however, especially in the case of a patient under continual treatment, thus making the measurement process tedious, frequent, and difficult to manage. Conventional measurement techniques require lancing of a convenient part of the body (normally a fingertip) with a sharp lancet, milking the finger to produce a drop of blood at the impalement site, and depositing the drop of blood on a measurement device (such as an analysis strip). This lancing method is painful, messy and inconvenient for the patient.

In order to minimize the time and cost for manual handling of taking specimen as well as the stress related to such manual handling on the laboratory animal or human subject, attempts have been made at automating the sample taking procedure.

However, most of the existing sampling systems usually suffer from at least one of the following limitations. The systems are not portable and their functioning depends either on gravity or a certain system orientation. Some systems suffer from possible sample carry-over from one sample to subsequent. In others, the sample is diluted with a rinsing fluid but the use of the rinsing fluid to limit carryover from one sample to another also leads to wastage of some sample fluid. In some other systems, the samples require some form of manual treatment such as pipetting, dilution or centrifugation before being introduced into the analysis device. In other systems, the samples require cooling or freezing to minimize possible analyte deterioration. Also, individual samples may be destroyed, lost or contaminated between sampling and analysis and in some systems; the samples are not immediately ready for shipment or storage. Further, a minimum sample volume of typically 50 micro liters is necessary to enable handling of sample in some other systems.

Therefore, there exists a need for a body fluid sampling device that overcomes the limitations of the existing systems and allows portability, continual sampling of the fluids, easy storage and handling and automatic preparation and analysis of the collected sample.

SUMMARY OF THE INVENTION

According to an embodiment of the invention, a body fluid sampling device is disclosed. The device includes a channel for allowing passage of the fluid through the channel, a flow controller for maintaining flow of the fluid in the channel; a flow direction controller for changing the direction of the flow of the fluid towards a collection medium; and the flow controller for delivering a portion of the fluid as a sample onto the collection medium.

According to another embodiment of the invention, the invention discloses a method for sampling a body fluid. The method includes passing the fluid through a channel; maintaining flow of the fluid in the channel using a fluid controller; changing the direction of the flow of the fluid towards a collection medium; and delivering a portion of the fluid as a sample onto the collection medium using the fluid controller.

BRIEF DESCRIPTION OF THE ACCOMPANYING FIGURES

The embodiments of the invention, together with its advantages, may be best understood from the following detailed description taken in conjunction with the accompanying figures in which.

DETAILED DESCRIPTION OF THE INVENTION

Figure 1:
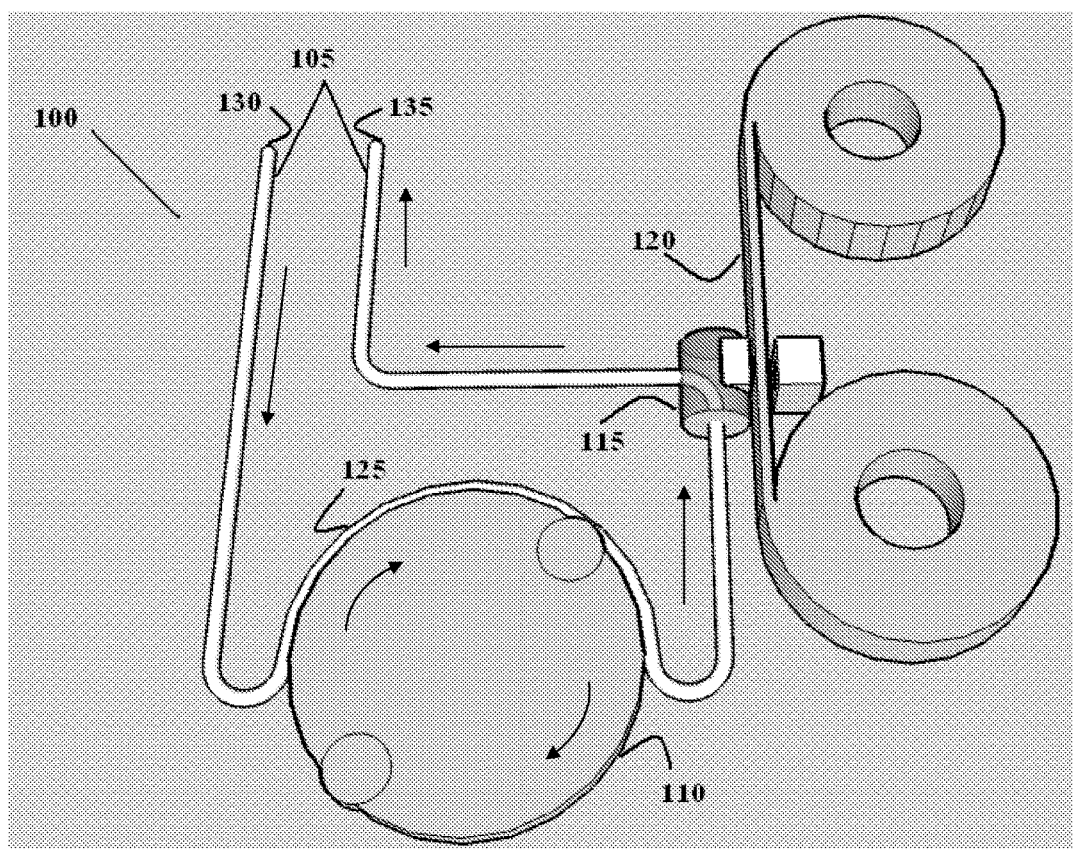
FIG. 1 illustrates a body fluid sampling device according to an embodiment of the invention.

The invention relates to a method and device for collection, storing, treatment/preparation and analysis of fluid samples such as but not limited to biological fluids. The fluid may include blood, gastrointestinal content, urine, cerebrospinal fluid, saliva and in other situations, the fluid may include industrial fluids from fermentation and chemical reactors, and fluids from natural sources such as sea water, streams, rivers, precipitation, aquifers and other sources such as sludge and sewage by depositing the sample on a collection medium, which is moved and exposed to a channel part of the channel carrying the fluid. The medium may be contained in a cassette for easy handling and prevention of contamination and the analysis may be performed by directly subjecting the collection medium to a known analysis method.

The device and method of the invention may be used in situations where the collection and storing may be from sources/subjects where volume of fluid available is very limited such as small animals or small flows of fluid in industrial, natural or biological systems. Also, the device may be used where other means of sampling (collection) from humans or animals may disturb the subject or influence the measurements.

The invention is now described below with the help of accompanying figures. It would be appreciated by the people skilled in the art that same feature of component of the device are referred with the same reference numeral in different figures.

According to an embodiment of the invention, a body fluid sampling device is disclosed. FIG. 1 illustrates the body fluid sampling device according to the embodiment of the invention. The device 100 includes a channel 105 for allowing passage of the fluid through the channel, a flow controller 110 for maintaining flow of the fluid in the channel 105; a flow direction controller 115 for changing the direction of the flow of the fluid towards a collection medium 120; and the flow controller for delivering a portion of the fluid as a sample onto the collection medium 120.

The portion of fluid is the amount that allows analysis of the sample. Typically the portion of the fluid is in the range of 5 to 25 microliter, preferably 15 microliter. However, it is also possible to have the portion to include either more than 25 microliter or less than 5 microliter, in other embodiments of the invention. The portion of fluid is usually a function of the minimum fluid required for analysis purposes.

The end 130 is connected to a subject, such as a patient or animal, for withdrawing the fluid out of the patient. The end 135, in one embodiment returns the fluid back to the subject, hence forming a closed loop of fluid flow. The direction along the channel shows the direction of fluid flow. In an alternative embodiment, the end 135 delivers the fluid to a fluid collector, such as a waste container, hence forming an open loop of fluid flow. In other embodiments, the fluid may be delivered to other fluid collectors, for example, to a receptacle of fluid analysis equipment. An actuation system (shown later), which is a part of the fluid direction controller.

Figure 2:
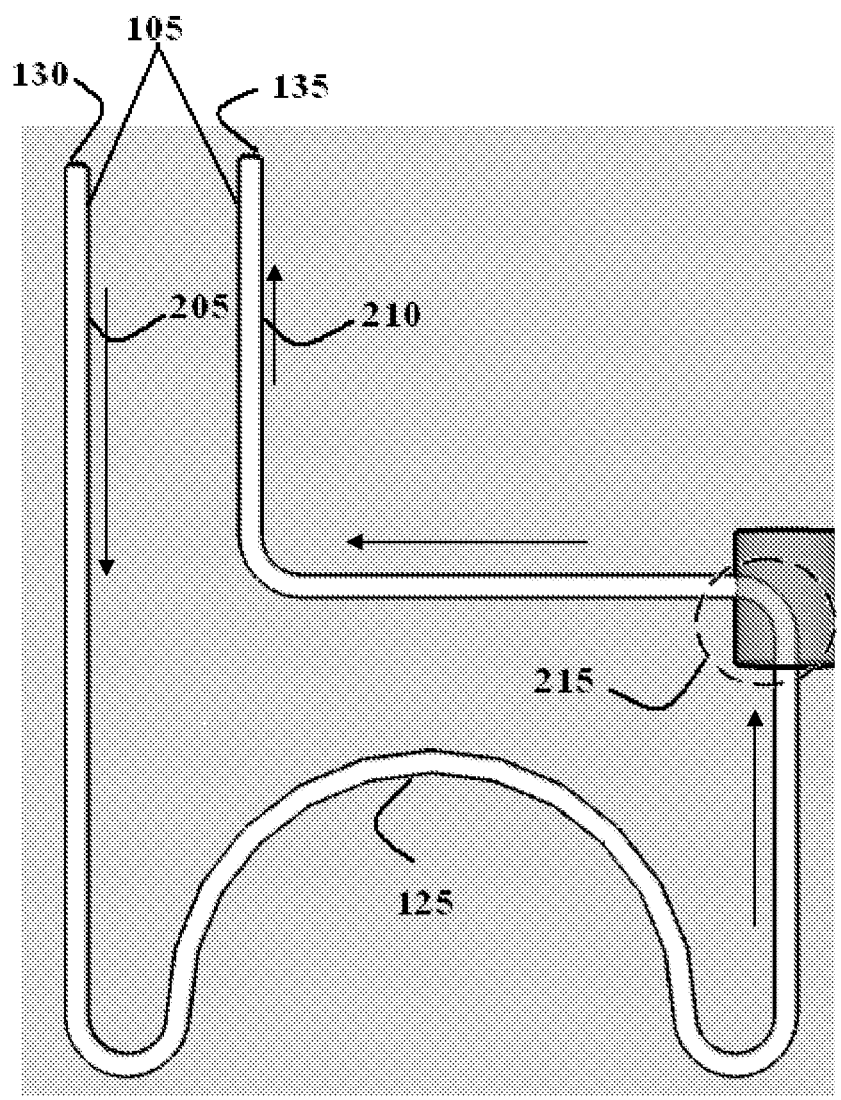
FIG. 2 illustrates the channel according to an embodiment of the invention.

Referring now to FIG. 2, the channel according to an embodiment of the invention is disclosed. The channel 105 includes a flexible tube, such as a catheter tube. The channel 105 includes an inflow channel 205, an outflow channel 210 and a channel part 215, which is positioned between the inflow channel 205 and the outflow channel 210.

In another embodiment, the channel may also include passage in housing of the sampling device for carrying the fluid, thus defining the inflow channel and outflow channel. The channel part may be defined by a passage in a rotatable cylinder, which is adapted to provide fluid connection between the inflow channel and the outflow channel. Flexible tube, interacting with a peristaltic pump (flow controller), may be used as the curvature tube portion connected to the passage defining the inflow channel. The circular direction indicated in the flow controller of FIG. 1 shows the direction of rotation of the peristaltic pump to enable flow of the fluid from the inflow channel towards the channel part. Alternatively, other pumping means may also be used irrespective of whether the flexible tube is being used.

In an embodiment of the invention, the inflow channel 205 includes a curvature tube portion 125. The curvature tube portion interacts with the flow controller (Refer FIG. 1, 110), which maintains the flow of fluid in the channel. The flow controller comprises a pump, such as a peristaltic pump. In other embodiments of the invention, other pumping means for maintaining flow of the fluid in the channel may also be used. It would be understood by the skilled person that the curvature tube portion only represents one embodiment of the invention. In other embodiments, the curvature tube portion may not be required if other pumping means do not preferably require such curvature for maintaining the flow of fluid in the channel and for delivering the fluid onto the collection medium. For example, the tube portion of the channel may alternatively be linear, that is a linear tube portion, to accommodate a linear peristaltic pump, which acts as the flow controller. The linear tube portion and the linear peristaltic pump are described later in the application.

FIG. 3 illustrates the channel part in a first position and a second position according to an embodiment of the invention. The flow direction controller 115, such as a valve, includes the channel part 215 controlled by an actuation means 140. The actuation means is adapted to position the channel part in at least two positions, that is, a first position and a second position.

The valve includes a cylindrical rotating member 115 and a flexible conduit having an afferent part, a slit and an efferent part, with the efferent part passing tangentially through a groove in said rotating member and where the afferent and efferent parts are fixed to the housing at a distance from the rotating member to allow 45 degrees to 180 degrees rotation of the member, and where the housing in one position of the member the efferent conduit is pressed against the housing creating a knick and closing the efferent flow while at the slit the conduit is bent so as to open the slit, and where the member in another position straightens out the knick of the efferent conduit and bends the afferent conduit with the slit in the opposite direction causing the slit to close.

Figure 3A:
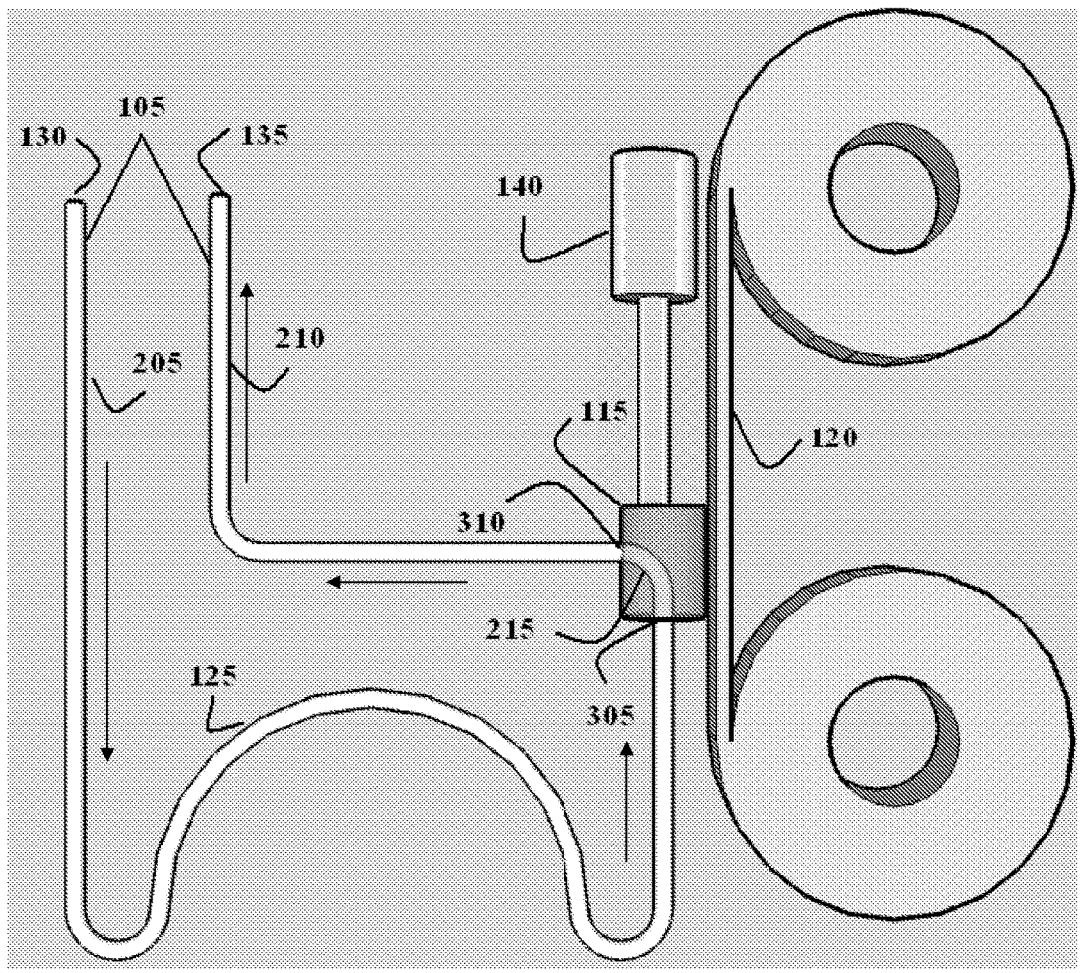
FIG. 3 illustrates the channel part and in (A) the channel part being in a first position and in (B) the channel part being in a second position, according to an embodiment of the invention.
Figure 3B:
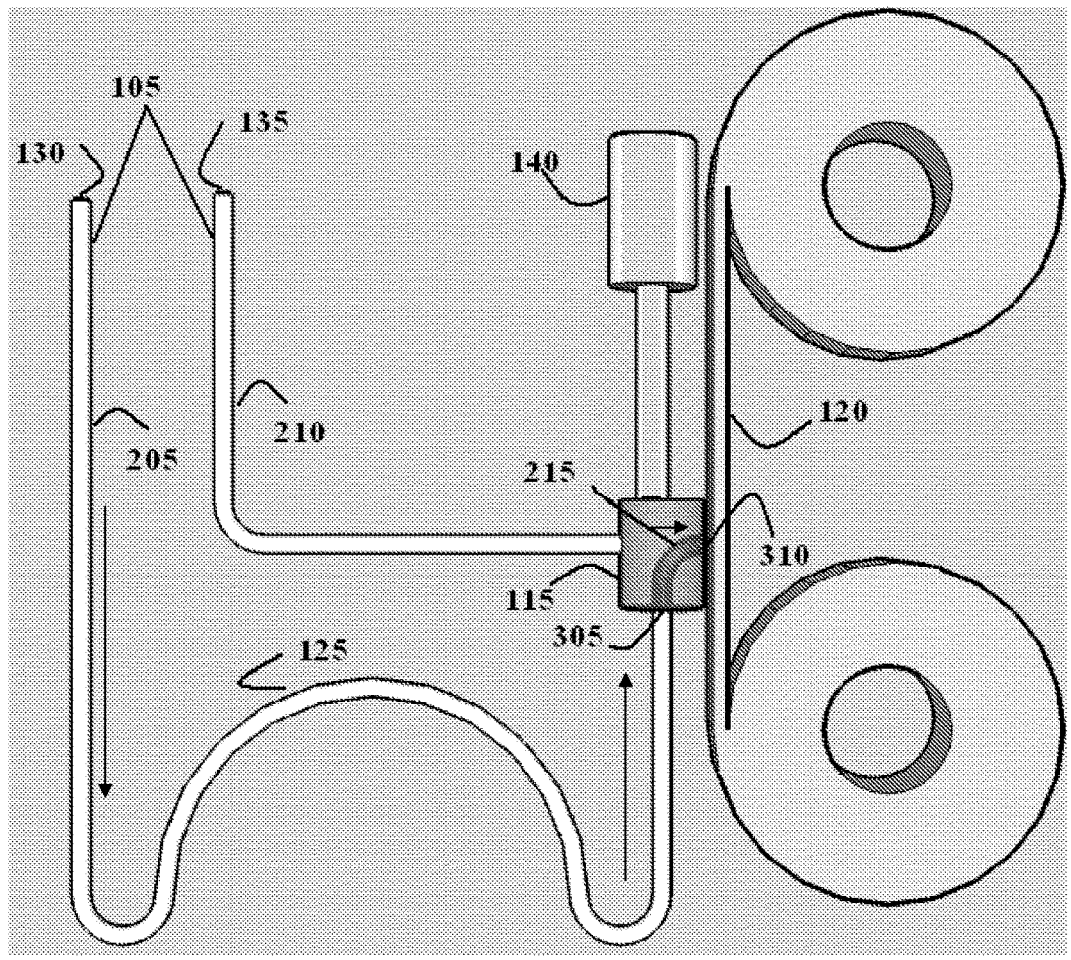

In the second position, the channel part faces the collection medium 120 and allows delivery of the portion of the fluid as the sample onto the collection medium (FIG. 3B). In one embodiment, the channel part 215 forms a closed loop of fluid flow in the channel when positioned in the first position (FIG. 3A). The closed loop is defined by the flow of fluid from a subject body via 130 through the channel 105 and back to the subject via 135. However, in another embodiment (not shown), the channel part 215 returns the fluid to the outflow channel 210, which in turn delivers the fluid to fluid collectors via 135, thereby forming an open loop instead.

The flow controller (Refer FIG. 1, 110), interacting with the tube curvature 125, compresses the curvature tube portion 125 of the inflow channel for maintaining the flow in the channel and for delivering the portion of fluid from the outflow end of the channel part onto the collection medium when the channel part is in the second position.

For example, in a typical peristaltic pump based flow controller, the pump includes a rotor with a number of rollers attached to external circumference of the rotor, which compresses the flexible curvature tube portion. As the rotor turns, the part of the tube under compression occludes, thus forcing the fluid to be pumped to move through the channel. As the channel opens (decompresses) to its natural state after the passing of the roller, fluid flow is induced by the peristaltic pump. Continuous operation of the peristaltic pump, thus maintains the flow of the fluid in the channel.

Figure 13A:
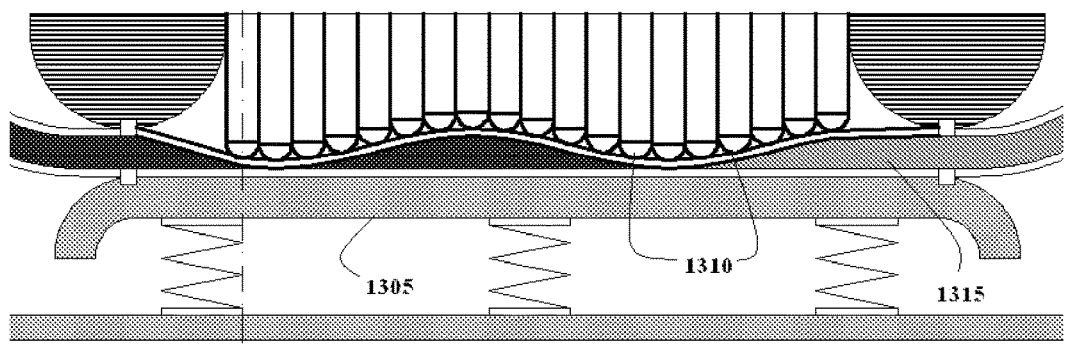
FIG. 13 illustrates, in FIG. 13(A) a cross-sectional view of linear peristaltic pump showing plurality of fingers and in FIG. 13(B) another cross-sectional view of a finger operatively connected to a cam lobe in the linear peristaltic pump, according to an embodiment of the invention.
Figure 13B:
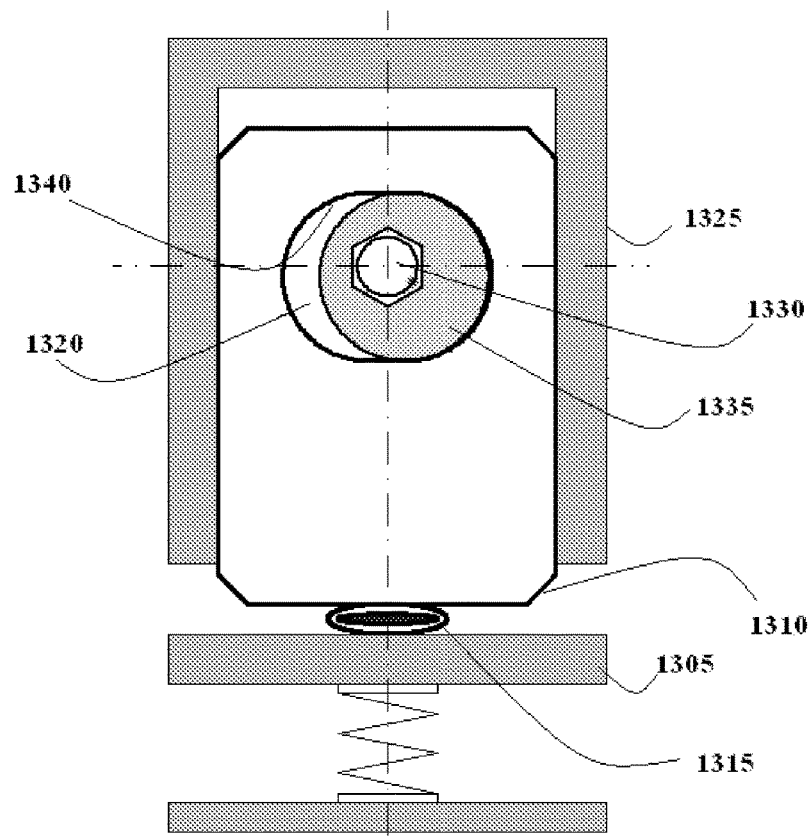

In another embodiment, as shown in FIG. 13, it is also possible for the flow controller 110 to include a linear peristaltic pump, where the linear tube portion 1315 rests against a platen 1305, which is part of the cassette. As is well know by the skilled artisan, peristaltic mechanisms require positioning of the tube portion between the platen and the peristaltic pump to allow compression of the tube portion. As shown in FIG. 13A, in this engagement, the linear tube portion 1315 is positioned between the platen 1305 and linear peristaltic pump to allow compression of the linear tube portion 1315 by fingers 1310. Now referring to FIG. 13B, where for simplicity reasons, all fingers and cam lobes will be referred to generally as 1310 and 1335, respectively. It is seen that each of the individual fingers 1310 are formed with an aperture 1320 to receive an individual cam lobe 1335 therein. Each finger 1310 is mounted in casing 1325 for movement in a direction substantially perpendicular to the longitudinal axis of camshaft 1330. The rotation of camshaft 1330 rotates each eccentrically mounted cam lobes 1335 so that it is urged against respective wall portions 1340 of the aperture 1320 to cause a reciprocal motion of finger 1310 within the casing 1325. As will be appreciated by those skilled in the pertinent art, cam lobes 1335 are eccentrically mounted on camshaft 1330 in a helical pattern along the axis of camshaft 1330 and are engaged with finger 1310 in a manner which creates a wave-like movement of fingers generally designated as 1330 when camshaft 1330 is rotated (shown in FIG. 13A), thereby maintaining flow of the fluid in the channel.

The main advantages of this kind of pump are simplicity and cleanliness in usage. Further and more importantly, fragile body fluid cells, such as blood cells are not damaged by this kind of pump. Nevertheless, it would be appreciated by the skilled person that other pumping means may also be utilized in the invention.

The inflow channel 205 of the channel receives the fluid from a subject, such as a patient or any test animal. The channel part 215 allows delivery of the portion of the fluid as the sample onto the collection medium when the channel part is in the second position (FIG. 3B); and in one embodiment, the outflow channel 210 takes the fluid back to the subject, thereby forming the closed loop, when the channel part is in the first position (FIG. 3A). In equally preferred embodiment, the outflow channel may deliver the returned fluid to a fluid collector, thereby forming the open loop.

The channel part is also illustrated in FIG. 3, according to an embodiment of the invention. The channel part 215 includes an inflow end 305 and an outflow end 310. The inflow end 305 receives the fluid from the inflow channel 205 in both the first position and the second position (FIGS. 3A and 3B). The outflow end 310 allows delivery of the sample onto the collection medium 120 when the channel part 215 is in the second position, i.e. the outflow end 310 faces collection medium (FIG. 3B), and provides the fluid back to the subject through the outflow channel 210, thereby forming the closed loop, when the channel part 215 is in the first position, i.e. the outflow end 215 is aligned with the outflow channel 210 (FIG. 3A).

In another embodiment of the invention, the inflow end is a continuous part of the inflow channel. In case, pumping means include the peristaltic pump, the inflow end, as part of the inflow channel is positioned after the curvature tube portion. The outflow end may be defined by a slit in the channel and positioned after the inflow end.

In yet another embodiment, where the channel is a passage in the rotatable cylinder, which is adapted to connect the inflow channel with outflow channel, the outflow end is the end in the passage of the rotatable cylinder from where the fluid flows out of the cylinder. In the second position, the fluid is delivered as the sample onto the collection medium. The inflow end is a peripheral passage in a part of the periphery of the cylinder, allowing inflow of the fluid from the inflow channel both in the first position and the second position, both positions being obtained by rotating the cylinder. The extremes of the peripheral passage with respect to the periphery of the cylinder are defined by the rotation needed to change the outflow end from the first position to the second position. The peripheral passage links to the outflow end using a diametric passage passing across and within the cylinder.

In different embodiments of the invention, the actuation means 140 for controlling the position of the channel part is selected from a manual mechanism and an automatic mechanism. Both the manual mechanism and the automatic mechanism are adapted to control the positioning of the channel part based on a predetermined parameter such as time difference between two samples, or a specific time when the sample is to be collected, etc.

The manual actuation mechanism 140 may include a manually operable physical means or a manually operated electronic device, which in turn sends command signal to a means in the system for changing the positioning of the channel part from one position to another. The automatic mechanism may include a processing unit adapted to send command signal to the means in the system for changing the position of the channel part based on predetermined parameters, such as time delays between two samples, volume of sample collected, time for the channel part to be in the second position, etc. The means usually includes a motor, such as a DC motor connected to the channel part via a gear system, such as a rack-and-pinion system or via a drive belt system. Typically, the actuation mechanism takes around one second to change the position from the first position to the second position and vice versa.

In another embodiment of the invention, the device may include a flow meter, which measures rate of flow of the fluid in the channel. The measured rate of flow may be used to calibrate the actuation means to position the channel part in the second position for a time period required to obtain a desired volume of the sample.

Figure 4:
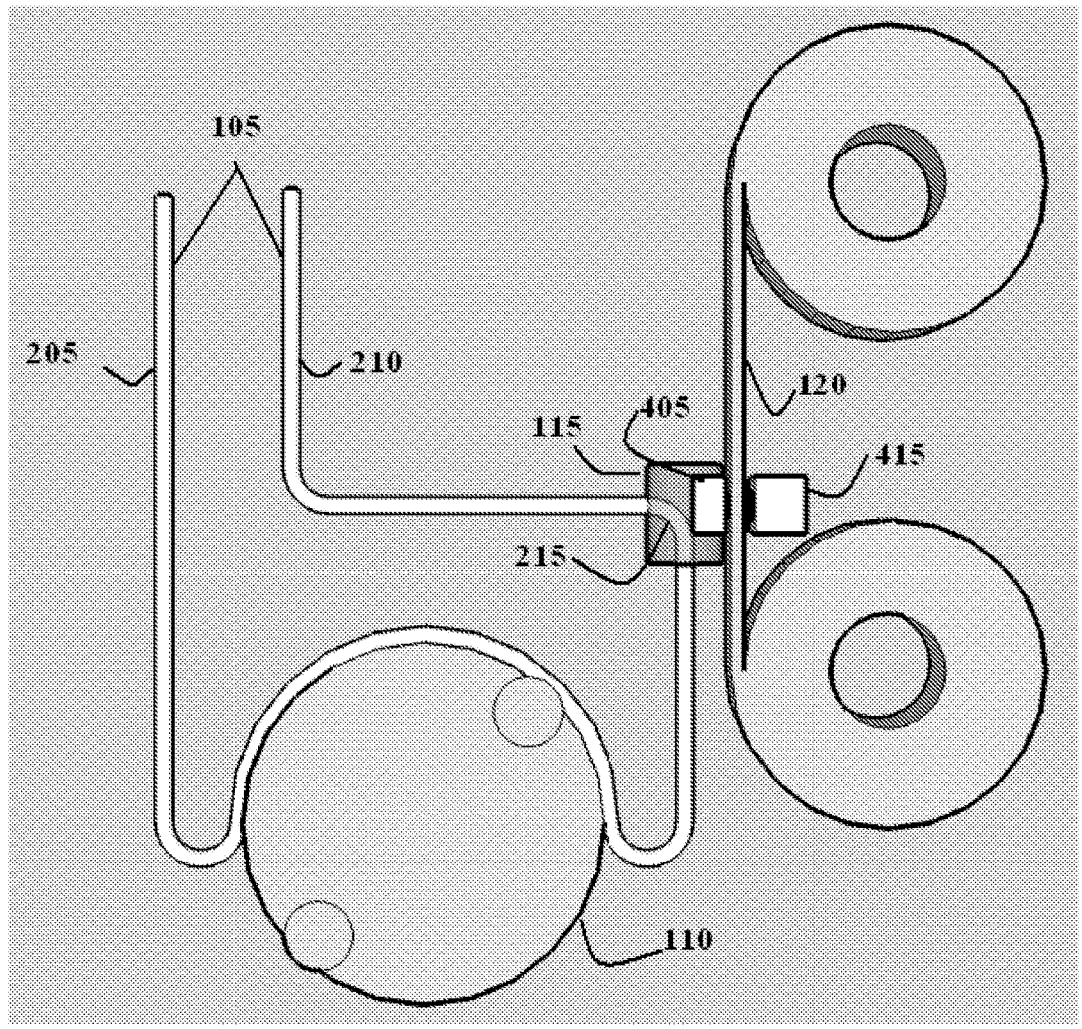
FIG. 4 illustrates the device comprising an illumination means and a detector according to an embodiment of the invention.

In order to determine the volume of sample collected, the device of the invention according to another embodiment as illustrated in FIG. 4 includes an illuminating means 405, such as at least one Light Emitting Diode (LED) for illuminating a sample area 410 on the collection medium 120, a detector 415, such as a miniature digital camera, for detecting a signal from the sample area; and a processor (not shown) coupled with the detector for processing the signal and determining properties, such as sample volume by measuring change of absorption in each pixel, associated with the sample. The sample area is defined by the area of the collection medium on which the sample is deposited. Further, the device is capable of transmitting the detected signal to the processor, which may be provided on the device or in other portable type devices, external to the device.

Other qualitative and quantitative properties may also be identified and analyzed based on the detected signal.

The collection medium is made up of an absorbent material, which allows absorption of sample deposited on the collection medium. In various embodiments of the invention, the collection medium is selected from a roll, tape, string, disc and pockets for each sample on the collection medium.

In an embodiment, the collection medium may be a cellulose paper. In other embodiments, the absorbent material may include a thin layer of collagenous or other gel or porous material or layers of different materials with different properties or the medium may consist of or contain organic molecules such as 2,5-dihydroxy benzoic acid, 3,5-dimethoxy-4-hydroxycinnamic acid, 4-hydroxy-3-methoxycinnamic acid, 3-hydroxy picolinic acid, 1-Thioglycerol, 2',5'-Dihydroxyacetophenone, 2,5-Dihydroxybenzoic acid, 2-Mercaptobenzothiazole, 2-Nitrophenyl octyl ether, 3-Nitrobenzyl alcohol, Glycerol, Isovanillin, Nicotinic acid, Perfluorokerosene, Salicylamide, Sinapic acid, Sinapinic Acid, α-Cyano-4-hydroxycinnamic acid, trans-Cinnamic acid. The collection medium may also consist of cellulose or SDS-PA. Possibly one layer of the collection medium may have highly hydrophilic properties allowing reduction of the water activity in other layers of the tape. The collection medium may contain aprotinin to prevent degradation of protein and peptides.

In some embodiments, the collection medium includes a composition to allow molecules to diffuse to different depths in the collection medium depending on chemical, biological or physical properties of the recording medium. The recording medium may also contain specific labeled or unlabeled antibodies or combinations of antibodies directed towards analytes to allow lateral flow through zones of different antibodies and reactants.

Figure 5:
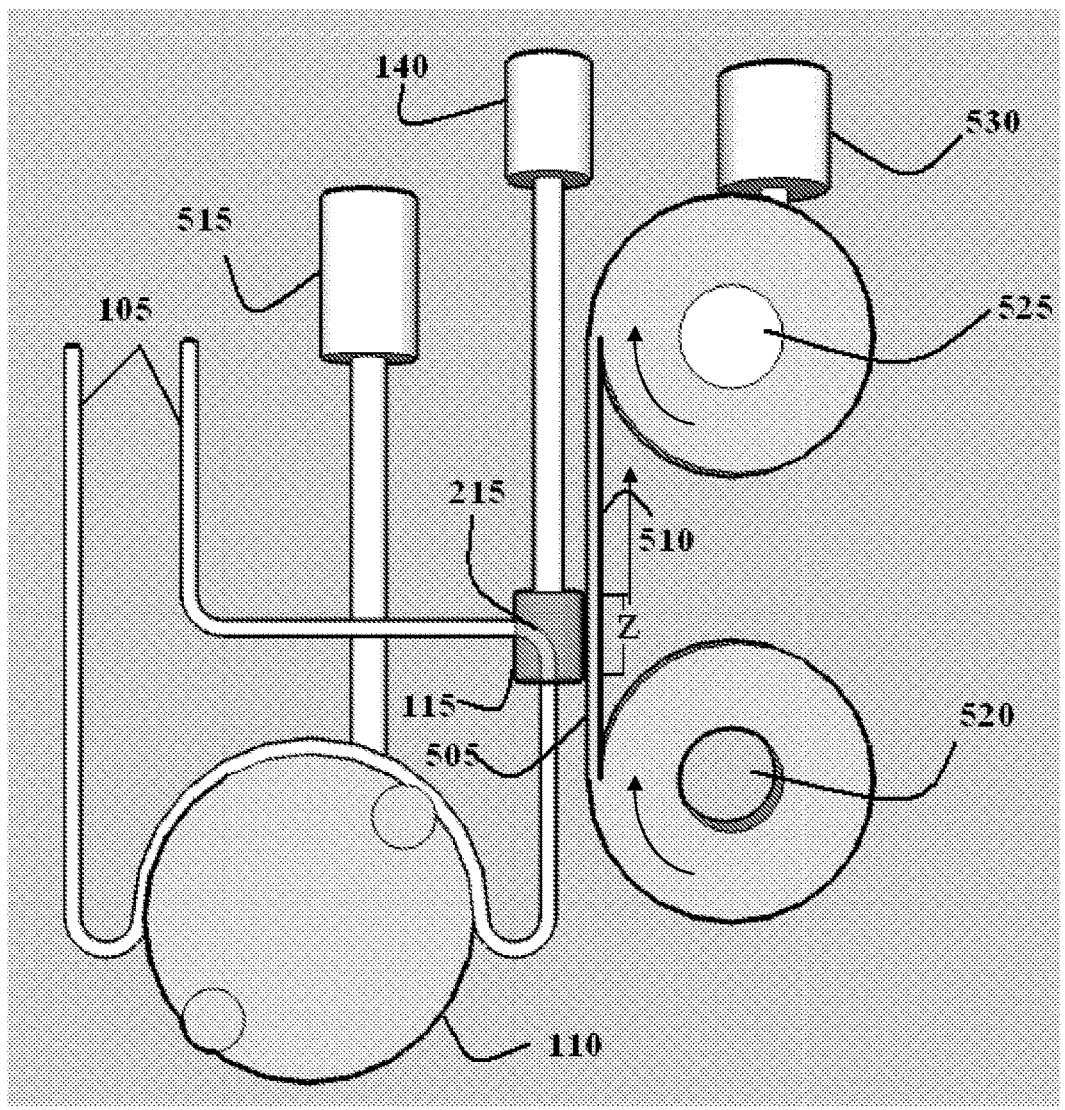
FIG. 5 illustrates set up of a collection medium according to an embodiment of the invention.

FIG. 5 illustrates set up of a collection medium according to an embodiment of the invention. The collection medium 120 comprises an unused collection medium 505 and a used collection medium 510. The used collection medium includes the collection medium containing the sample 515.

In an embodiment of the invention, the unused collection medium 505 is rolled around an unused bobbin 520 and the used collection medium 510 is rolled around a used bobbin 525. The used bobbin is connected to a drive means 530, which rotates the used bobbin 525 such that the collection medium 505 unrolls from the unused bobbin 520 and the used collection medium 510 rolls around the used bobbin 525. the direction in this figure shows the direction of movement of the collection medium and the rotation direction of the used bobbin and the unused bobbin. The unrolled collection medium is passed across and exposed to the outflow end of the channel part 215 and collects the sample onto the exposed unused collection medium (shown by zone Z); and the used collection medium 510 rolls around the used bobbin 525. The drive means may be operated to either continuously or intermittently rotate the used bobbin, resulting in either continuous or intermittent movement of the collection medium across the outflow end of the channel part. The drive means usually includes a motor, such as a DC motor connected to the channel part via a gear system, such as a rack-and-pinion system or via a drive belt system. One would appreciate that in an embodiment of the invention, the same DC motor may be used for the means coupled with the actuation system and also for the drive means. The figure also shows the actuation means 140, which is adapted to change the position of the direction flow controller 115 from the first position to the second position and vice versa.

Further, flow controller drive means 515 is also shown. The flow controller drive means controls and drives the flow controller and may include any conventional means, which allows operation of the flow controller such as a peristaltic pump.

In an embodiment, the used bobbin is enclosed within the unused bobbin. The collection medium, which is a roll, runs from the unused bobbin to the used bobbin when the drive means rotates the used bobbin and the collection medium on its way from the unused bobbin to the used bobbin is exposed to the channel part for sample deposition. In another embodiment of the invention, the unused bobbin is enclosed within the used bobbin. However, the drive means still drives the used bobbin and moves the collection medium from the unused bobbin to the used bobbin and the collection medium collects the sample on its way from the unused bobbin to the used bobbin. The embodiments are described later in FIG. 6.

In yet another embodiment of the invention, the unused coil and the used coil are positioned without one coil being enclosed by another (see FIG. 5). For example, the unused bobbin and the used bobbin may be placed along an axis and the collection medium moves from the unused bobbin to the used bobbin under the influence of a pulling force produced by the driving means, which rotates the used bobbin. The collection medium is exposed to the sample on its way from the unused bobbin to the used bobbin.

Figure 6:
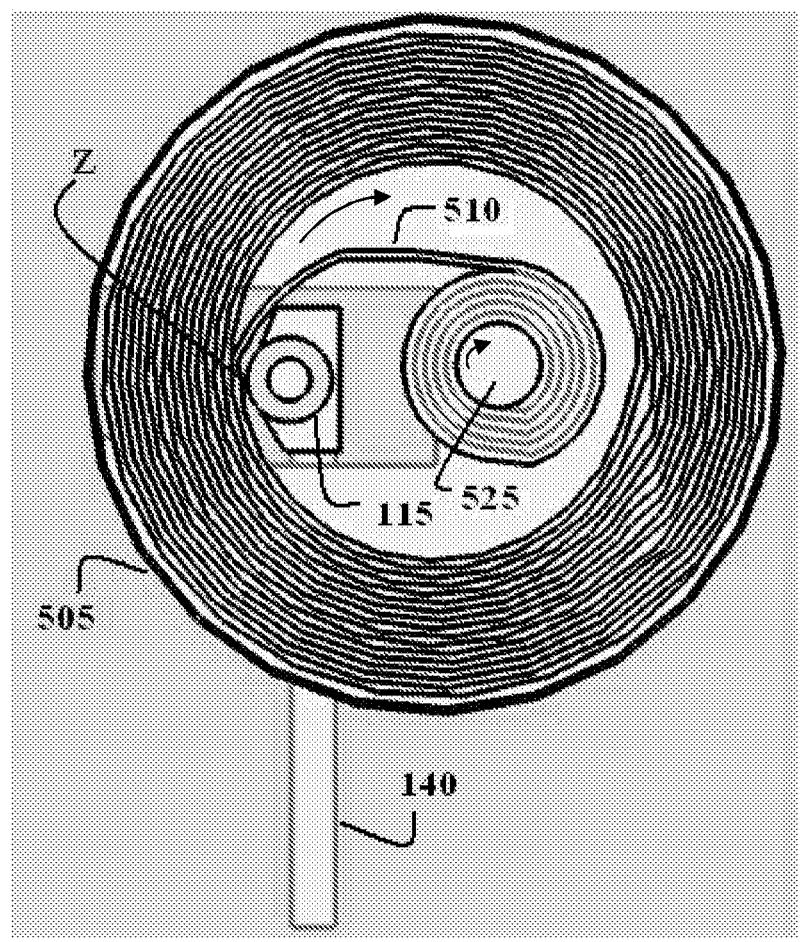
FIG. 6 illustrates a compact sample recording medium according to an embodiment of the invention.

FIG. 6 illustrates a compact sample recording medium according to an embodiment of the invention. The recording medium includes an unused bobbin comprising an unused collection medium rolled 505 around the unused bobbin, an used bobbin 525 adapted to rotate and comprising a used collection medium 510 rolled around the used bobbin. The direction in the figure shows the rotational direction of the used inner bobbin 525 and the unused outer bobbin. The unused collection medium unrolls from the unused bobbin and is exposed to the fluid and collects the sample in zone Z, and moves towards used bobbin as a used collection medium. The used bobbin is enclosed within the unused bobbin, as shown in FIG. 6. In another embodiment of the invention, the unused bobbin is enclosed within the used bobbin, but in principle represents recording medium similar to that in FIG. 6 except the positioning of the used bobbin and the unused bobbin is interchanged. Also, the drive means rotating the outer used bobbin in this embodiment will rotate the used bobbin in a direction, which allows unrolling of the unused medium from the unused bobbin. 140 represent the actuation system, which is a part of the fluid direction controller and 115 represents the flow direction controller for changing the direction of the flow of the fluid towards a collection medium 520.

In yet another embodiment of the invention, the collection medium includes a disc. The disc includes a collection surface area. The disc is coupled to a motor, which rotates the disc in steps in such a way that with each actuation, the disc exposes an unused disc area to the outflow end of the channel part. The sample is delivered on to the exposed disc area and once the sample is collected, the motor rotates the disc to expose a yet another unused disc area for sample collection. In various embodiments, the samples are collected as concentric circles, circles with continuously reducing radius with one end at the centre and the other close to the periphery of the disc, etc.

Figure 7:
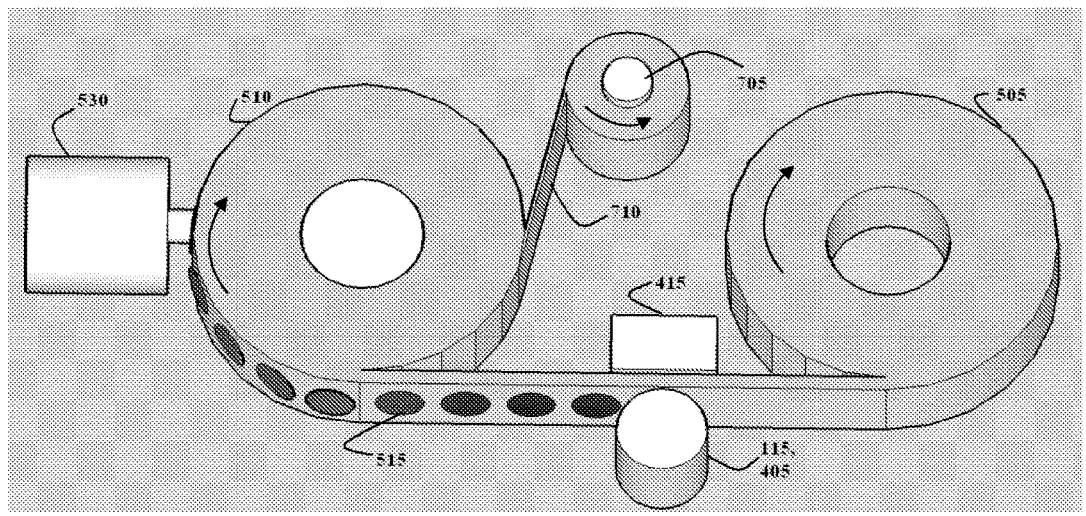
FIG. 7 illustrates a separating film coil according to an embodiment of the invention.

FIG. 7 illustrates a separating film coil according to an embodiment of the invention. The separating film coil 705 provides a reagents/protective layer 710 over the sample area 515 of the used collection medium 510 to prevent contamination of the sample. The drive means 530, which rotates the used bobbin, creates pulling force for unrolling the protective layer 710 from the separating film coil and rolling the protective layer over the used collection medium 510. The rotational direction of used bobbin, unused bobbin and the separating film coil is shown by the included directions. In an alternative embodiment, the device may include a reagent applicator applying the reagent on the used recording medium, more particularly on the sample area of the used recording medium, which protects the sample from contamination. The figure also illustrates the flow direction controller 115 and the illumination means 405 along with the detector 415. The illumination means-detector combination allows determining properties of the sample based on the signal detected from the sample area 515. Although, the FIG. 7 illustrates the separating film coil for a collection medium set up where one bobbin is not enclosed in another bobbin. However, person skilled in the art would appreciate that the device may be modified easily to use the principle of the separating film coil and the reagent applicator in the compact recording medium of the FIG. 6 as well.

Figure 8:
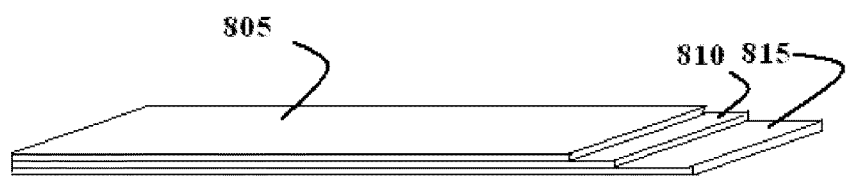
FIG. 8 illustrates the collection medium according to an embodiment of the invention.

In yet another embodiment of the invention, FIG. 8 illustrates the collection medium. The recording medium may include layers of a porous material 805, a hydrophilic material 810 and a magnetic tape 815. The magnetic layer 815 allows for storing digital data. Further the collection medium may include markings, such as barcode or datamatrix markings on the tape for identification of individual samples.

Figure 9A:
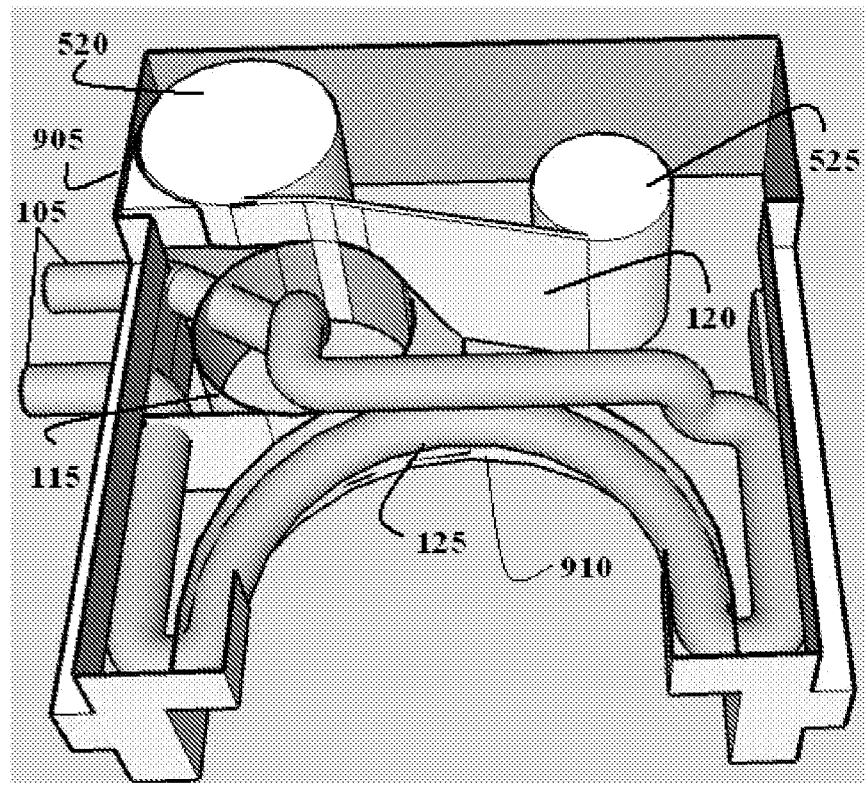
FIG. 9 illustrates a cassette according to an embodiment of the invention.

FIG. 9 illustrates a cassette according to an embodiment of the invention. In FIG. 9A, the device includes a cassette 905, which includes the channel 105, flow direction controller 115, curvature tube portion 125, collection medium 120, unused bobbin 520, and used bobbin 525. The curvature tube portion rests against a curved platen 910, which forms part of the cassette. In another embodiment of the invention, the cassette further comprises the flow controller. In yet another embodiment, the cassette includes the channel 105, flow direction controller 115, and curvature tube portion 125. The cassette of this particular embodiment may also include the flow controller.

Figure 9B:
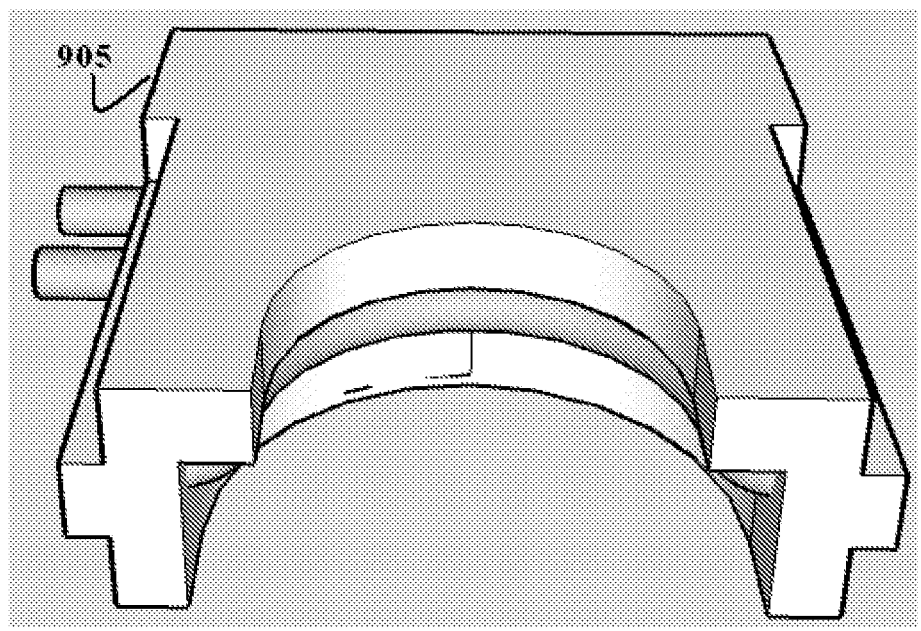

The cassette is sealable and is sealed as shown in FIG. 9B and is sterilizable and disposable. The cassette is easily transportable. The cassette may contain a digital storage media for identification of the collection medium and may also contain data relating to the sample. In case, the entire collection medium has been used or the sample is to be collected from a different subject, the cassette is removed and is replaced by a new cassette. When the sample has been collected, the cassette may be stored, shipped, pre-treated or analysed.

In an embodiment of the invention, where some form of pre-treatment or preparation is required before analysis, the cassette with the sample is inserted in an apparatus that performs treatment of the medium. The treatment may include but not limited to extraction of analyte by solvents, electrical current, digestion or dissolution of the matrix for subsequent analysis of the resulting solution, removal of inorganic ions by washing, ion substitution or other means, removal of water or other solvent from the sample by freeze-drying, application of solutions containing immunological reactants such as specific antibodies, application of luciferase in combination with relevant enzymes and reactants for measurement of components in the sample such as glucose, application of one or more specific antibodies directed towards analytes. These could be linked with enzymes to generate color change, fluorescence or other detectable reactions.

When the cassette with collection medium is ready for analysis, the cassette is inserted into a cassette device that, in one embodiment, feeds a loop of the used collection medium into an analysis device. If the analysis device uses laser ionisation, then the used collection medium is exposed to the laser. In other embodiments, the analysis device could use techniques such as LC-MS, MS, LDI-MS, MALDI-MS, MS/MS, MALDI-TOF, MALDI-TOF/TOF, HPLC, fluorescence measurements or absorbance measurements or combinations of these. In yet another embodiment, the used collection medium is cut into fragments or samples are punched from the tape and placed in tubes, vials or microtitre plates and the analyte is extracted for analyses by an appropriate solvent, and the resulting solution analyzed conventionally.

Figure 10:
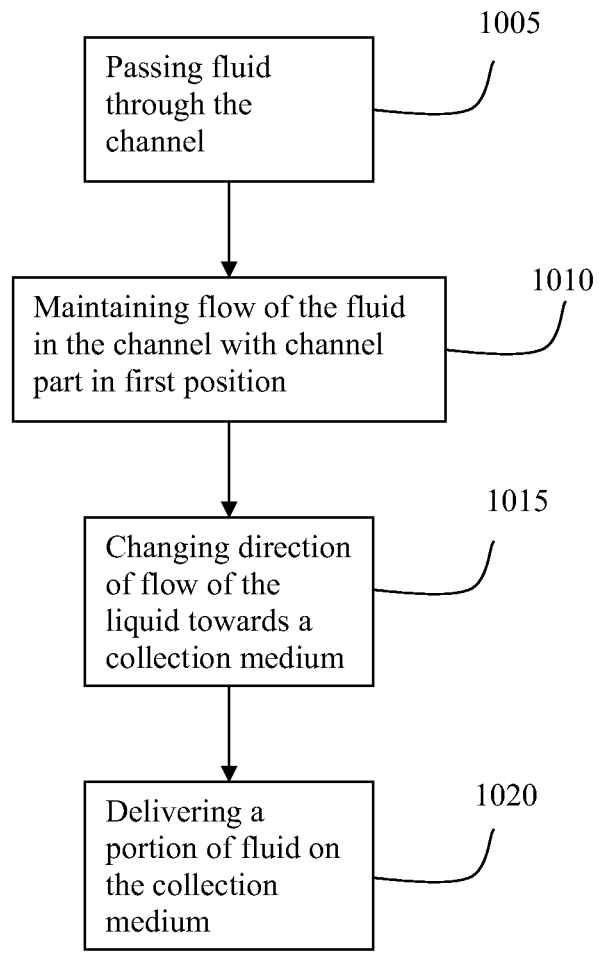
FIG. 10 illustrates a method for sampling a fluid according to an embodiment of the invention.

According to an embodiment of the invention, a method for sampling a fluid is disclosed in FIG. 10. The method includes passing the fluid through a channel at 1005; maintaining flow of the fluid in the channel using a fluid controller at 1010; changing the direction of the flow of the fluid towards a collection medium at 1015; and delivering a portion of the fluid as a sample onto the collection medium using the fluid controller at 1020.

Figure 11:
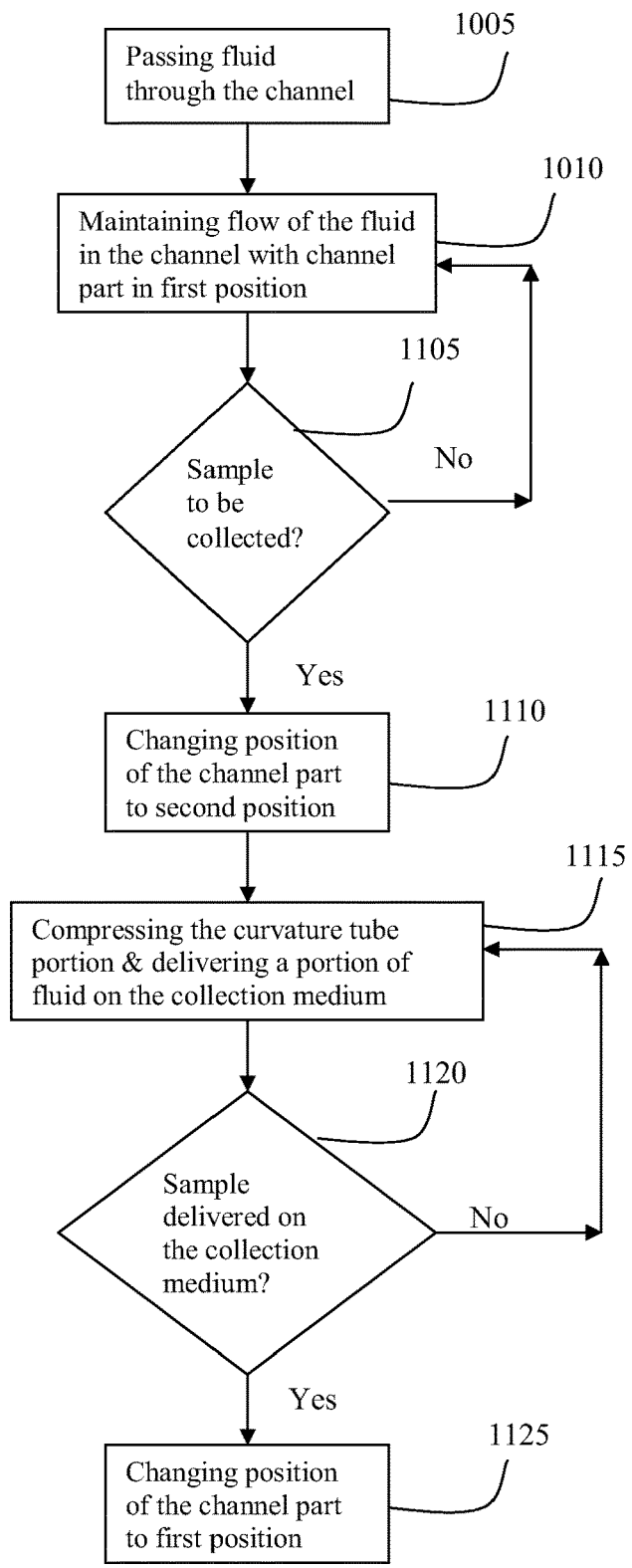
FIG. 11 illustrates a method for sampling a fluid according to another embodiment of the invention.

FIG. 11 illustrates additional steps of the method for sampling the fluid according to another embodiment of the invention. The method includes steps 1005 and 1010 of FIG. 10. At 1010, the channel part is in the first position, thus forming a closed loop. The closed loop is defined by the flow of fluid from a subject body through the channel and back to the subject. However, in an alternative embodiment, the channel may form an open loop even when the channel part is in the first position by delivering the fluid through the outflow channel to a fluid collector, as described earlier. Thereafter, a determination is made at 1105 whether the sample is to be collected. Such determination may be based on parameters such as time delays between collections of consecutive samples, etc. If so, then at 1110, the position of the channel part is changed from the first position to a second position. In the second position, the outflow end of the channel part faces the collection medium. At 1115, the curvature tube portion of the channel is compressed using the flow controller, which allows delivery of the portion of the fluid as the sample onto the collection medium. Additionally, a determination may be made at 1120, if the sample was delivered to the collection medium. If no, then the compression of the curvature tube portion is continued using the flow controller. However, if the sample is delivered, then at 1125, the channel is positioned back to the first position, thereby again forming a closed loop.

The method described above includes controlling the position of the channel part using the flow direction controller in at least two positions such that in a first position the channel part forms a closed loop of fluid flow in the channel and in a second position the channel part faces the collection medium and allows delivery of the portion of the fluid as the sample onto the collection medium. In addition, the method includes compressing a curvature tube portion of the inflow channel using the flow controller for maintaining the flow in the channel and for delivering the portion of fluid from an outflow end of the channel part onto the collection medium when the channel part is in the second position.

In an embodiment of the invention, the method includes rotating a used bobbin using a drive means such that the collection medium unrolls from an unused bobbin having the unused collection medium and the used collection medium rolls around the used bobbin. The method also includes unrolling the unused collection medium from the unused bobbin, passing across and exposing the unused collection medium to the channel part and collecting the sample on the exposed unused collection medium; and rolling the used collection medium around the used bobbin.

Figure 12:
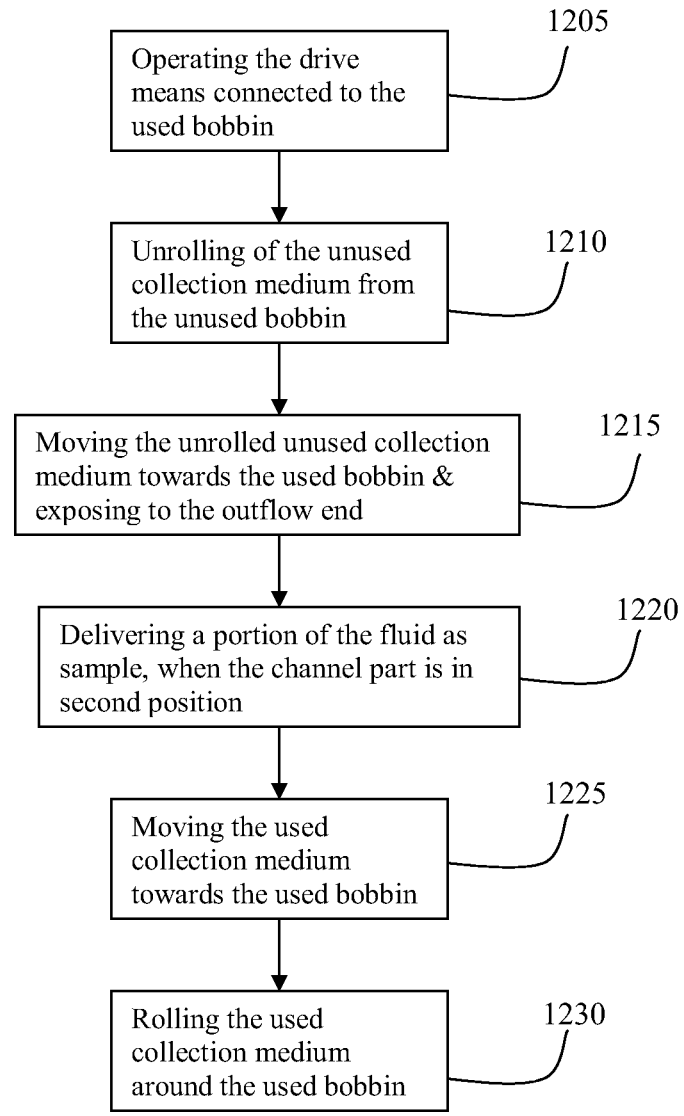
FIG. 12, illustrates movement of the collection medium according to an embodiment of the invention.

These features of the invention are exemplified in FIG. 12, which illustrates movement of the collection medium according to an embodiment of the invention. When the sample is to be collected, the drive means, connected to the used bobbin, is operated at 1205 to rotate the used bobbin. This creates a pulling force in the collection medium towards the used bobbin, resulting in unrolling of the unused collection medium from the unused bobbin at 1210. At 1215, the unrolled unused collection medium moves from the unused bobbin towards the used bobbin. The unrolled unused collection medium, on its way towards the used bobbin is exposed to the outflow end of the channel part, with the channel part being in the second position, and the portion of the fluid is delivered as the sample at 1220. Once the sample is delivered onto the collection medium, the collection medium with the sample (used collection medium) is moved towards the used bobbin at 1225, where the used collection medium is rolled around the used bobbin at 1230.

In an additional embodiment of the invention, the method includes illuminating a sample area on the collection medium using an illuminating means, the sample area being defined by the area of the collection medium on which the sample is deposited; detecting a signal from the sample area using a detector; and processing the signal using a processor coupled with the detector for determining properties, such as sample volume, associated with the sample.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Throughout the foregoing description, for the purposes of explanation, numerous specific details were set forth in order to provide a thorough understanding of the invention. It will be apparent, however, to one skilled in the art that the invention may be practiced without some of these specific details.

Accordingly, the scope and spirit of the invention should be judged in terms of the claims which follow.

I claim:

1. A fluid sampling device comprising:
a channel arranged to allow passage of a fluid through the channel, the channel having an inflow end to receive the fluid and an outflow end to expel the fluid, the outflow end being different from the inflow end, the inflow and outflow ends defining a unidirectional flow of the fluid to form a closed loop, and wherein the inflow end is adapted to be attached to a subject to receive fluid from the subject, and the outflow end is adapted to be attached to the same subject to return the fluid to the same subject;
a single flow controller configured to maintain the unidirectional flow of the fluid in the channel; and
a flow direction controller having a first position forming the closed loop of the unidirectional flow of the fluid and a second position, the second position of the flow direction controller configured to change direction of the unidirectional flow of the fluid from being directed toward the outflow end to being directed toward a collection medium; so that
the single flow controller is configured to deliver a portion of the fluid as a sample onto the collection medium when the flow direction controller is in the second position, wherein the fluid sampling device includes only the single flow controller that provides the unidirectional flow of the fluid.

2. The device according to claim 1, wherein the channel is selected from a flexible tube and a passage within a housing of the device.

3. The device according to claim 1, wherein the channel includes an inflow channel, an outflow channel and a channel part positioned between the inflow channel and the outflow channel, the inflow channel having the inflow end and the outflow channel having the outflow end.

4. The device according to claim 3, wherein the inflow channel comprises a curvature tube portion, the curvature tube portion interacts with the single flow controller, which maintains the unidirectional flow of the fluid in the channel.

5. The device according to claim 1, wherein the single flow controller comprises a pump.

6. The device according to claim 1, wherein the flow direction controller comprises a channel part controlled by an actuation means, the actuation means being adapted to position the channel part in at least two positions such that in a first channel position the channel part forms the closed loop of unidirectional flow of the fluid in the channel and in a second channel position the channel part faces the collection medium and allows delivery of the portion of the fluid as the sample onto the collection medium.

7. The device according to claim 1, wherein the flow direction controller comprises a channel part controlled by an actuation means, the actuation means being adapted to position the channel part in at least two positions such that in a first channel part position the channel part forms an open loop of fluid flow in the channel and in a second channel part position the channel part faces the collection medium and allows delivery of the portion of the fluid as the sample onto the collection medium.

8. The device according to claim 1, wherein the flow direction controller comprises:
a cylindrical rotating member; and
a flexible conduit having an afferent part, a slit and an efferent part, with the efferent part passing tangentially through a groove in said rotating member and where the afferent and efferent parts are fixed to a housing of the device at a distance from the rotating member to allow 45 degrees to 180 degrees rotation of the rotating member, and
where the housing in one position of the rotating member, the efferent part is pressed against the housing creating a knick and closing efferent flow while at the slit the flexible conduit is bent so as to open the slit, and
where the rotating member in another position straightens out the knick of the efferent part and bends the afferent part with the slit in an opposite direction causing the slit to close.

9. The device according to claim 4, wherein the single flow controller compresses the curvature tube portion of the inflow channel for maintaining the unidirectional flow in the channel and for delivering the portion of the fluid from an outflow end of the channel part onto the collection medium when the channel part is in the second position.

10. The device according to claim 3 wherein: the inflow channel is adapted to receive the fluid from the subject; the channel part allows delivery of the portion of the fluid as the sample onto the collection medium when the channel part is in the second position; and the outflow channel is adapted to take the fluid back to the subject, thereby forming the closed loop, or forms an open loop, when the channel part is in the first position.

11. The device according to claim 3, wherein: the inflow end receives the fluid from the inflow channel in both the first position and the second position; and
the outflow end is adapted to provide the fluid back to the subject through the outflow channel, thereby forming the closed loop, or forms an open loop when the channel part is in the first position.

12. The device according to claim 6, wherein the actuation means is selected from a manual mechanism and an automatic mechanism, the mechanisms being adapted to control positioning of the channel part based on a predetermined parameter such as time difference between deliveries of two samples.

13. The device according to claim 1, wherein the collection medium is made up of an absorbent material and is selected from a group consisting of a roll, tape, string, disc and pockets for each sample on the collection medium.

14. The device according to claim 1, wherein the collection medium comprises an unused collection medium and a used collection medium comprising the collection medium containing the sample.

15. The device according to claim 14 wherein: the unused collection medium is rolled around an unused bobbin and the used collection medium is rolled around a used bobbin; and the used bobbin is connected to a drive means, which rotates the used bobbin such that the unused collection medium unrolls from the unused bobbin and the used collection medium rolls around the used bobbin.

16. The device according to claim 15 wherein: the unused collection medium unrolls from the unused bobbin, the unrolled unused collection medium is passed across and exposed to an outflow end of a channel part and collects the sample onto the exposed unused collection medium; and the used collection medium rolls around the used bobbin.

17. The device according to claim 15 wherein the used bobbin is enclosed within the unused bobbin.

18. The device according to claim 15 wherein the unused bobbin is enclosed within the used bobbin.

19. The device according to claim 15 wherein the unused bobbin and the used bobbin are positioned without one bobbin being enclosed by another.

20. The device according to claim 1, wherein the collection medium includes a disc, the disc comprising a collection surface area for collecting the sample and the disc being coupled to a motor that rotates the disc in steps in such a way that with each actuation, the disc exposes an unused disc area to an outflow end of a channel part.

21. The device according to claim 1, further comprising:
an illuminating means for illuminating a sample area on the collection medium,
the sample area being defined by an area of the collection medium on which the sample is deposited;
a detector for detecting a signal from the sample area; and
a processor coupled with the detector for processing the signal and determining properties associated with the sample.

22. The device according to claim 1, wherein the device comprises a cassette including the channel, the flow direction controller, and a curvature tube portion.

23. The device according to claim 1, wherein the device comprises a cassette including the channel, the flow direction controller, a curvature tube portion, the collection medium, an unused bobbin, and a used bobbin.

24. The device according to claim 22 wherein the cassette further comprises the single flow controller.

25. The device according to claim 22 wherein the cassette is sealable, sterilizable and disposable.

26. The device according to claim 1, further comprising a separating film coil providing at least one of reagents and a protective layer over a sample area to prevent contamination of the sample.

27. The device according to claim 3 wherein the inflow channel comprises a linear tube portion, the linear tube portion interacts with the single flow controller which maintains the unidirectional flow of the fluid in the channel.

28. The device according to claim 1, wherein the single flow controller is placed between the inflow and outflow ends of the channel defining the unidirectional flow of the fluid.

29. The device according to claim 1, wherein the single flow controller is placed between the inflow end and the flow direction controller.

30. A method for sampling a fluid, comprising:
passing the fluid through a channel having an inflow end to receive the fluid and an outflow end to expel the fluid, the outflow end being different from the inflow end, the inflow and outflow ends defining a unidirectional flow of the fluid to form a closed loop, and wherein the inflow end is adapted to being attached to a subject to receive fluid from the subject, and the outflow end is adapted to being attached to the same subject to return the fluid to the same subject;
maintaining the unidirectional flow of the fluid in the channel using a single fluid controller;
moving a flow direction controller between a first position forming the closed loop of fluid flow and a second position, in which the unidirectional flow of the fluid changes direction from being directed toward the outflow end to being directed toward a collection medium; and
delivering a portion of the fluid as a sample onto the collection medium using the single fluid controller when the flow direction controller is in the second position, the method using only the single fluid controller for maintaining the unidirectional flow of the fluid.

31. The method according to claim 30, wherein the channel includes an inflow channel, an outflow channel and a channel part positioned between the inflow channel and the outflow channel, the inflow channel having the inflow end and the outflow channel having the outflow end.

32. The method according to claim 30, further comprising controlling a position of a channel part using the flow direction controller in at least two positions such that in a first channel part position the channel part forms the closed loop of fluid flow in the channel and in a second channel part position the channel part faces the collection medium and allows delivery of the portion of the fluid as the sample onto the collection medium.

33. The method according to claim 30, further comprising controlling a position of a channel part using the flow direction controller in at least two positions such that in a first channel part position the channel part forms an open loop of fluid flow in the channel and in a second channel part position the channel part faces the collection medium and allows delivery of the portion of the fluid as the sample onto the collection medium.

34. The method according to claim 30, further comprising compressing a curvature tube portion of an inflow channel using the single fluid controller for maintaining the unidirectional flow in the channel and for delivering the portion of the fluid from an outflow end of a channel part onto the collection medium when the channel part is in the second position.

35. The method according to claim 30, wherein the collection medium comprises an unused collection medium and a used collection medium comprising the collection medium containing the sample.

36. The method according to claim 30, further comprising rotating a used bobbin using a drive means such that the collection medium unrolls from an unused bobbin having an unused collection medium and a used collection medium rolls around the used bobbin.

37. The method according to claim 30, further comprising: unrolling an unused collection medium from an unused bobbin, passing across and exposing the unused collection medium to a channel part and collecting the sample on the exposed unused collection medium; and rolling a used collection medium around a used bobbin.

38. The method according to claim 30, further comprising:

illuminating a sample area on the collection medium using an illuminating means, the sample area being defined by an area of the collection medium on which the sample is deposited; detecting a signal from the sample area using a detector; and processing the signal using a processor coupled with the detector for determining properties associated with the sample.

* * * * *